United States Patent
Zhou et al.

(10) Patent No.: US 7,485,859 B2
(45) Date of Patent: *Feb. 3, 2009

(54) CHARGED BEAM APPARATUS AND METHOD THAT PROVIDE CHARGED BEAM AERIAL DIMENSIONAL MAP

(75) Inventors: Lin Zhou, LaGrangeville, NY (US); Eric Peter Solecky, Hyde Park, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/736,191

(22) Filed: Apr. 17, 2007

(65) Prior Publication Data
US 2008/0258055 A1    Oct. 23, 2008

(51) Int. Cl.
*G01R 27/00* (2006.01)
*F41G 1/30* (2006.01)

(52) U.S. Cl. .................. 250/306; 250/526; 356/634; 356/635

(58) Field of Classification Search ........... 250/397, 250/396 ML, 492.2, 251, 310, 491.1; 430/5, 430/30, 296
See application file for complete search history.

(56) References Cited
U.S. PATENT DOCUMENTS

| | | | |
|---|---|---|---|
| 4,517,488 A | 5/1985 | Say | |
| 4,535,266 A | 8/1985 | Say | |
| 4,683,366 A | 7/1987 | Harte et al. | |
| 5,182,492 A | 1/1993 | Chen | |
| 6,232,787 B1* | 5/2001 | Lo et al. | 324/751 |
| 6,861,793 B2 | 3/2005 | Sakurai et al. | |
| 7,019,293 B1* | 3/2006 | Hamada | 250/310 |
| 2003/0132765 A1* | 7/2003 | Yamada et al. | 324/702 |
| 2003/0233870 A1* | 12/2003 | Mancevski | 73/105 |
| 2005/0116726 A1* | 6/2005 | Yamada et al. | 324/702 |
| 2005/0194534 A1* | 9/2005 | Kneedler et al. | 250/307 |
| 2007/0187595 A1* | 8/2007 | Tanaka et al. | 250/307 |
| 2008/0067373 A1* | 3/2008 | Zhou et al. | 250/310 |

* cited by examiner

*Primary Examiner*—Nikita Wells
*Assistant Examiner*—Johnnie L Smith, II
(74) *Attorney, Agent, or Firm*—Scully, Scott, Murphy & Presser, P.C.; Rosa B. Suazo Yaghmour, Esq.

(57) ABSTRACT

A charged beam apparatus, such as an electron microscopy apparatus, and a method for determining an aerial dimensional map of a charged beam within the charged beam apparatus, each use a test structure that includes a feature located upon a substrate. One of the feature and the substrate is conductive and the other of the feature and the structure is non conductive. The charged beam within the charged beam apparatus is scanned in a plurality of non-parallel linear directions with respect to the substrate and the feature to provide a corresponding plurality of current versus position response curves from which may be determined the aerial dimensional map of the charged beam within the charged beam apparatus.

8 Claims, 2 Drawing Sheets

CHARGED BEAM APPARATUS AND METHOD THAT PROVIDE CHARGED BEAM AERIAL DIMENSIONAL MAP

BACKGROUND

1. Field of the Invention

The present invention relates generally to charged beam apparatus and methods, such as but not limited to electron beam apparatus and methods. More particularly, the present invention relates to charged beam aerial dimensional mapping within charged beam apparatus and methods.

2. Description of the Related Art

Within the microelectronic fabrication art, accurate measurement of a dimension of a given feature within a microelectronic structure is often critical for process control and yield learning. Commonly, the dimension of such a feature may be measured using an electron microscopy apparatus and method. Electron microscopy apparatus and methods use accelerated electrons that are focused into an electron beam that is used as a measurement probe with respect to a microelectronic feature located within or upon a microelectronic substrate. Within electron microscopy apparatus and methods, such an electron beam is often scanned across a particular feature within a microelectronic substrate. As a result of the interaction of electrons within the electron beam with a material from which is comprised the particular feature, a dimension of the particular feature may often be readily determined.

While electron microscopy apparatus and methods are common in the microelectronic fabrication art, electron microscopy apparatus and methods are nonetheless not entirely without problems. In particular, since electron microscopy apparatus and methods are predicated upon an interaction of an electron beam with a material from which is comprised a particular feature within a microelectronic structure, aerial dimensions of a particular electron beam within a particular electron microscopy apparatus and method may often be of particular importance in assuring that the dimension of the particular feature is accurately determined.

As is common in the microelectronic fabrication art, microelectronic feature dimensions within microelectronic structures are certain to continue to decrease as microelectronic structure and microelectronic device fabrication technology advances. Thus, desirable are charged beam apparatus and methods, such as in particular electron microscopy apparatus and methods, that provide for enhanced microelectronic feature dimension measurement precision and measurement accuracy as microelectronic feature dimensions decrease.

SUMMARY OF THE INVENTION

The invention includes a charged beam apparatus, such as but not limited to an electron microscopy apparatus, that is configured for determining an aerial dimensional map of a charged beam, such as an electron beam, used within the charged beam apparatus. The invention also includes a method for determining the aerial dimensional map of the charged beam within the charged beam apparatus, such as but not limited to the electron beam within the electron microscopy apparatus.

A method in accordance with the invention uses a test structure that includes a feature located upon a substrate, where the substrate and the feature have different electrical conductivity characteristics (i.e., typically one of the feature and the substrate comprises a conductive material and the other of the feature and the substrate comprises a non-conductive material). A charged beam within the charged beam apparatus is scanned using a plurality of non-parallel linear directions (i.e., at least in part mutually intersecting linear directions) with respect to both the substrate and the feature. At least one intersection point of the plurality of non-parallel linear directions is typically, but not necessarily exclusively, located within the feature. A plurality of electric current versus position response curves for the charged beam is measured for the plurality of non-parallel linear directions, and based upon analysis of the plurality of current versus position response curves an aerial dimensional map of the charged beam may be determined.

A charged beam apparatus in accordance with the invention is programmed to scan the charged beam with respect to the test structure described above in the plurality of non-parallel linear directions. The test structure may be fabricated as a test substrate separate from the charged beam apparatus. Alternatively, the test structure may be fabricated integral to the charged beam apparatus.

A particular charged beam apparatus in accordance with the invention includes a charged beam source that emits a charged beam directed towards a test structure comprising a feature located upon a substrate. The substrate and the feature have different electrical conductivity characteristics. The charged beam is programmed to scan across the substrate and the feature in a plurality of non-parallel linear directions. This particular charged beam apparatus also includes a means for measuring a current through at least one of the substrate and the feature as a function of a position of the charged beam in each of the plurality of non-parallel linear directions.

A particular electron microscopy apparatus in accordance with the invention includes an electron beam source that emits an electron beam directed towards a test structure comprising a feature located upon a substrate. The substrate and the feature have different electrical conductivity characteristics. The electron beam is programmed to scan the substrate and the feature in a plurality of non-parallel linear directions. This particular electron microscopy apparatus also includes a means for measuring a current through at least one of the feature and the substrate as a function of a position of the electron beam in each of the plurality of non-parallel linear directions.

A particular method for determining an aerial dimensional map of a charged beam in accordance with the invention includes providing a test structure comprising a feature located upon a substrate. The feature and the substrate have different electrical conductivity characteristics. This particular method also includes scanning a charged beam in a plurality of non-parallel linear directions with respect to the substrate and the feature and measuring through at least one of the feature and the substrate a current as a function of a position the charged beam for each of the plurality of non-parallel linear directions. This particular method also includes determining an aerial dimensional map of the charged beam from the measurement of the current versus the position of the charged beam for each of the plurality of non-parallel linear directions.

BRIEF DESCRIPTION OF THE DRAWINGS

The objects, features and advantages of the invention are understood within the context of the Description of the Preferred Embodiment, as set forth below. The Description of the Preferred Embodiment is understood within the context of the accompanying drawings, which form a material part of this disclosure, wherein.

DESCRIPTION OF THE PREFERRED EMBODIMENT

The invention, which includes: (1) a charged beam apparatus such as an electron microscopy apparatus; as well as (2) a method for determining an aerial dimensional map of a charged beam used within the charged beam apparatus such as the electron microscopy apparatus, is understood within the context of the description that follows. The description that follows is understood within the context of the drawings described above. Since the drawings are intended for illustrative purposes, the drawings are not necessarily drawn to scale.

Figure 1:
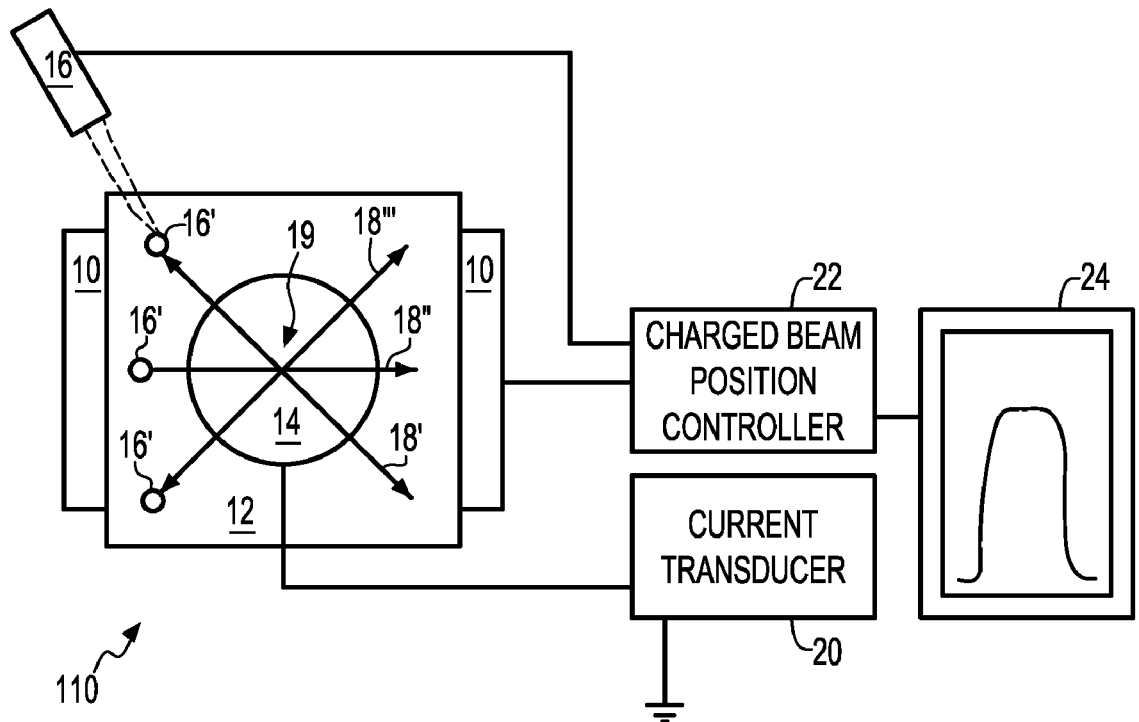
FIG. 1 shows a schematic diagram of an apparatus in accordance with a particular embodiment of the invention.

FIG. 1 shows a schematic diagram of a charged beam apparatus in accordance with a particular embodiment of the invention. While this particular embodiment is directed most particularly towards determining an aerial dimensional map of an electron beam within an electron microscopy apparatus, neither the instant embodiment nor the invention is necessarily so limited. Rather, the instant embodiment and the invention contemplate modifications of the instant embodiment, as well as possible alternative embodiments, for determining an aerial dimensional map of a charged beam within a charged beam apparatus. In particular the embodiment and the invention are applicable to determining an aerial dimensional map of either a negative charged beam or a positive charged beam within a charged beam apparatus. Such negative charged beams and positive charged beams may include, but are not limited to, electron beams, negative ion beams and positive ion beams. Similarly, such charged beams, whether they comprise negative charged beams or positive charged beams, may be used within any of several types of charged beam apparatus. Particularly included, but also not limiting, are charged beam metrology apparatus and charged beam material processing apparatus. Such charged beam apparatus may be used within microelectronic fabrication applications including but not limited to semiconductor fabrication applications, ceramic substrate fabrication applications and optoelectronic fabrication applications.

FIG. 1 first shows platen 10 and a charged beam source 16 that comprise part of a charged beam apparatus in accordance with the instant embodiment. Within this instant embodiment, at least one of the platen 10 and a charged beam that emanates from the charged beam source 16 is intended to be at least in part movable with respect to the other of the platen 10 and the charged beam that emanates from the charged beam source 16 so that (as is disclosed further below) the charged beam that emanates from the charged beam source 16 may be scanned with respect to a test structure. In accordance with the instant embodiment, the test structure (as is also disclosed in further detail below) may be provided as a separate test substrate component from the charged beam apparatus. However, the instant embodiment is not necessarily so limited. Rather, for example and without limitation, such a test structure may in fact be fabricated as an integral component of the platen 10, or alternatively as an other associated component within a charged beam apparatus in accordance with the embodiment and the invention.

Although not specifically illustrated within the schematic diagram of FIG. 1, the charged beam source 16 and the platen 10 are both typically located within an enclosure that is maintained under vacuum (i.e., usually from about 1.0E-5 to about 3.0E-7 torr with 1.0E-6 torr being more typical) so that the charged beam that emanates from the charged beam source 16 is not otherwise influenced by environmental factors.

The platen 10 may be fabricated from any of several materials that are otherwise generally conventional in the charged beam apparatus fabrication art. Non-limiting examples include metals and metal alloys (such as in particular stainless steel alloys), as well as certain ceramic materials, ceramic alloy materials and related environmentally stable composites.

In accordance with disclosure above, the charged beam source 16 may provide either a positive charged beam or a negative charged beam. Negative charged beams are generally more common, and in particular electron beams as negative charged beams are most common. Other positive charged beams and negative charged beams that include positive ion charged beams and negative ion charged beams are also within the scope and context of the instant embodiment.

FIG. 1 also shows a test substrate 110 that includes a test structure. The test structure comprises a substrate 12 that includes a feature 14 located upon (which is also intended to include "within" in the context of the claimed invention) the substrate 12. The instant embodiment is operative under circumstances where one of the substrate 12 and the feature 14 is relatively conductive and the other of the substrate 12 and the feature 14 is relatively non-conductive. Thus, the substrate 12 and the feature 14 have different electrical conductivity characteristics. A conductive material from which may be comprised the conductive one of the substrate 12 and the feature 14 may include any of several metals, metal alloys and metal nitrides that may be laminated upon a non-conductive material. Other conductive materials are not excluded. A non-conductive material from which may be comprised the non-conductive one of the substrate 12 and the feature 14 may include any of several dielectric materials and semiconductor materials, as well as composites thereof and laminates thereof. Particular examples of substrates that may comprise the substrate 12 include semiconductor substrates, ceramic and other dielectric substrates, composites thereof and laminates thereof, including in particular top surface conductive material laminated laminates thereof.

The feature 14 may be formed upon the substrate 12 to provide the test structure using any of several methods that are conventional in the microelectronic fabrication art. Non-limiting examples include layer transfer methods, layer laminating methods, subtractive etch methods and selective deposition methods that may include, but are not limited to plating methods.

The feature 14 may in particular comprise any of several geometric shapes. Non-limiting examples include triangles, rectangles, squares, other regular and irregular polyhedra, regular and irregular non-polyhedra, ellipses and circles. In general, circles are particularly preferred since a circle as the feature 14 provides a most uniform feature with which to practice a method in accordance with the embodiment and the invention. Alternatively, if a charged beam (as described in further detail below) is expected, intended or designed to have other than a circular aerial dimensional map, the feature 14 may appropriately have other than a circular geometry. Typically, the feature 14 has a linewidth from about 5 to about 100 nanometers and a charged beam (as is described further below) will have a nominal linewidth from about 1 to about 5 nanometers.

As suggested above, FIG. 1 also shows a plurality of locations for a charged beam 16' (i.e., beam spots) each one of which is scanned with respect to both the substrate 12 and the feature 14 in a corresponding plurality of non-parallel linear directions 18', 18" and 18'". The plurality of non-parallel linear directions 18', 18" and 18'" mutually intersect at a single intersection point 19 that is nominally centered within the feature 14. However, such an intersection point (i.e., both single and within the feature 14) is not a limitation of the embodiment. The locations of the charged beam 16' and the scanning thereof in the plurality of non-parallel linear directions 18', 18" and 18'" typically derive from relative motion of the test substrate 110 and the platen 10 with respect to the charged beam source 16. However, such a particular mechanical scanning configuration does not limit the invention. As a non-limiting alternative, the charged beam source 16 may be fixed with respect to the test substrate 110 and the platen 10, and a scanning of the charged beam 16' along the plurality of non-parallel linear directions 18', 18" and 18'" may be effected using appropriate electromagnetic optical focusing and directing elements and components.

FIG. 1 also shows a current transducer 20 that is connected to the feature 14 under circumstances where the feature 14 comprises a conductive material rather than a non-conductive material. Alternatively, when the substrate 12 comprises a conductive material rather than the feature 14, the substrate 12 is connected to the current transducer 20. The current transducer 20 is intended to monitor a current from the conductive one of the substrate 12 and the feature 14, as appropriate, when the charged beam 16' is scanned with respect to the substrate 12 and the feature 14 in the corresponding plurality of non-parallel linear directions 18', 18" and 18'".

FIG. 1 also shows a charged beam position controller 22. The charged beam position controller 22 is intended to control the positions of the charged beam 16' when the charged beam 16' is scanned with respect to the substrate 12 and the feature 14 in each of the corresponding plurality of non-parallel linear directions 18', 18" and 18'".

FIG. 1 finally shows a plotter 24 that is used to plot a series of currents versus a series of positions for the charged beam 16' for each of the plurality of non-parallel linear directions 18', 18" and 18'". The resultant current versus position curves may be referred to as "current versus position response curves." In accordance with further disclosure below, such current versus position response curves are typically formatted to include current as an ordinate and charged beam position as an abscissa.

Although FIG. 1 illustrates the current transducer 20, the charged beam position controller 22 and the plotter 24 for purposes of determining a current versus position response curve for the charged beam 16' along each of the plurality of non-parallel linear directions 18', 18" and 18'", such a particular assemblage of signal processing components does not limit either the instant embodiment or the invention. Rather, other commercially available or custom components, including both hardware components and software components, are also contemplated by the instant embodiment, provided that such alternative components allow for determination of a current versus position response curve for the charged beam 16' along each of the plurality of non-parallel linear directions 18', 18" and 18'" when scanned across the substrate 12 and the feature 14.

Figure 2:
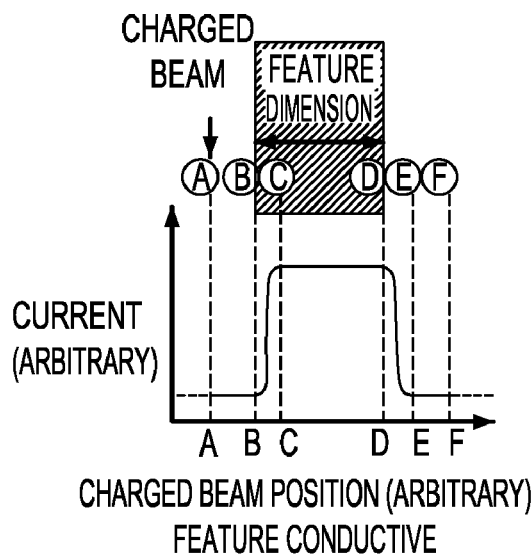
FIG. 2 and FIG. 3 show a pair of graphs of Current versus Charged Beam Position for charged beam scanning of a test structure including either a conductive feature located upon a non-conductive substrate (FIG. 2) or a non-conductive feature located upon a conductive substrate (FIG. 3), while using the charged beam apparatus whose schematic diagram is illustrated in FIG. 1.

FIG. 2 shows a graph of Current versus Charged Beam Position (i.e., a current versus position response curve) for the charged beam 16' scanning the substrate 12 and the feature 14 in any one of the plurality of non-parallel linear directions 18', 18" or 18'" that is illustrated in FIG. 1 (i.e., where the feature 14 comprises a conductive material). The A position and the F position denote a comparatively low or zero current when the charged beam 16' impinges upon the substrate 12 that comprises a non-conductive material. The portions of the plots that correspond with the increasing current transition from the B to C inflection points and the decreasing current transition from the D to E inflection points correspond to a transition of the charged beam 16' from the substrate 14 that comprises the non-conductive material to the feature 14 that comprises the conductive material, or the reverse. Typically, a maximum current at a C to D plateau within the graph of FIG. 2 is from about 1 to about 10 picoamps.

Figure 3:
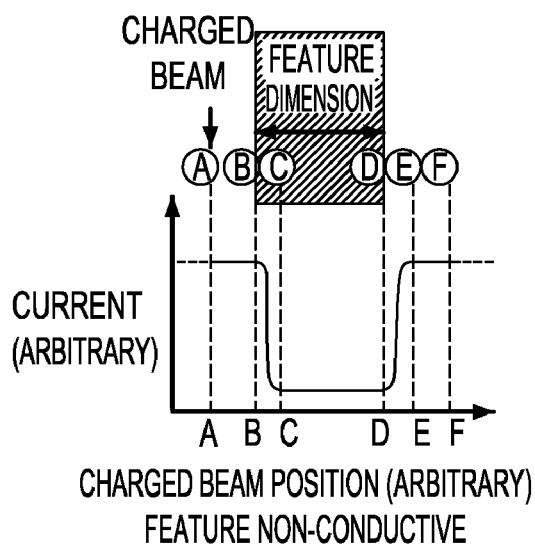

FIG. 3 shows a Current versus Charged Beam Position graph (i.e., a current versus position response curve) that corresponds with the Current versus Charged Beam Position graph of FIG. 2, but is intended to address the complementary alternative where the substrate 12 comprises a conductive material and the feature 14 comprises a non-conductive material. Under such circumstances, when the charged beam 16' impinges upon the substrate 12 a comparatively high current is observed rather than a comparatively low current. Similarly, the B to C and D to E transitions are also reversed in comparison with FIG. 2.

As is understood by a person skilled in the art, within the context of the data that are illustrated within the graphs of either FIG. 2 or FIG. 3, a charged beam 16' diameter in one of the particular corresponding non-parallel linear direction 18', 18" or 18'" that is illustrated in FIG. 1 may be obtained from the data of FIG. 2 or FIG. 3 as simply the difference of C-B, or the difference of E-D. Within the context of the instant embodiment, multiple measurements of C-B and E-D, and an average thereof, are desirable. This particular embodiment contemplates as desirable up to about 30 current versus position response curves in a particular non-parallel linear direction 18', 18" or 18'", to thus provide up to about 60 measurements for a charged beam 16' diameter in a particular non-parallel linear direction 18', 18" or 18'".

As is understood by a person skilled in the art, by using the data that is illustrated in FIG. 2 or FIG. 3 for each of the plurality of non-parallel linear directions 18', 18" and 18'" a diameter of the charged beam 16' in each of the plurality of non-parallel linear directions (i.e., an aerial dimensional map of the charged beam 16') may be determined. While the instant embodiment illustrates the invention within the context of three non-parallel linear directions 18', 18" and 18'", the invention is clearly not so limited. Rather, the embodiment and the invention may use a greater number of non-parallel linear directions (such as the non-parallel linear directions 18', 18" and 18'") to provide a more precise and accurate aerial dimensional map of a charged beam (such as the charged beam 16'). More particularly, the embodiment contemplates the use of up to about 180, and preferably from about 4 to about 180, and more preferably from about 8 to about 180, non-parallel linear directions in order to provide a more precise and accurate aerial dimensional map for a particular charged beam, such as the charged beam 16'.

The value of an increased number of non-parallel linear directions for measurement of a corresponding increased number of current versus position response curves that provide a more precise and accurate aerial dimensional map of a charged beam is illustrated in FIG. 4 to FIG. 7.

Figure 4:
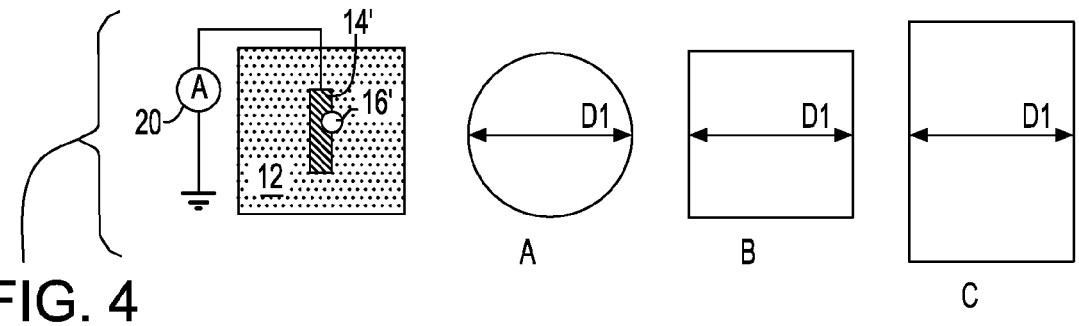
FIG. 4 to FIG. 7 show a series of schematic diagrams illustrating a plurality of test structures that may be used to determine an aerial dimensional map of a charged beam within a charged beam apparatus in accordance with the embodiment of the invention.

FIG. 4 shows, for example, the nominally circular charged beam 16' that is scanned across a nominally rectangular feature 14' that is located upon the substrate 12. As a result of a single scan in a single horizontal direction, a charged beam diameter D1 in the single horizontal direction is determined. Unfortunately, the charged beam diameter D1 in the single horizontal direction as determined in FIG. 4 provides insufficient information to provide a meaningful aerial dimensional map of the charged beam 16', since such a single horizontal dimension for the charged beam diameter D1 does not allow, for example, for distinction between a circle A, a rectangle B or a square C (as illustrated in FIG. 4) as an aerial dimensional map for the charged beam 16'.

Figure 5:
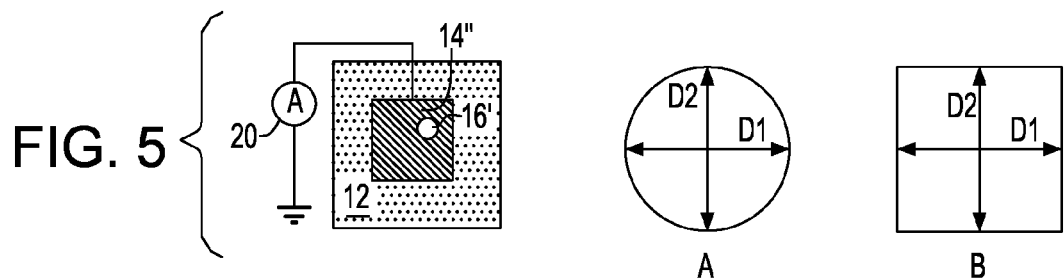

Within FIG. 5, a second vertical non-parallel linear direction is added to the single horizontal linear direction for the charged beam 16' scan of FIG. 4 (but where a feature 14" now comprises a square shape), to allow for determination of a charged beam diameter D2 in a vertical direction as well as the charged beam diameter D1 in the horizontal direction. As an illustrative example within the context of FIG. 5, the charged beam diameter D1 in the horizontal direction nominally equals the charged beam diameter D2 in the vertical direction, thus precluding a rectangle for the charged beam 16' aerial dimensional map, but still also not distinguishing between the circle A and the square B (or alternative plausible options) for the aerial dimensional map for the charged beam 16'.

Figure 6:
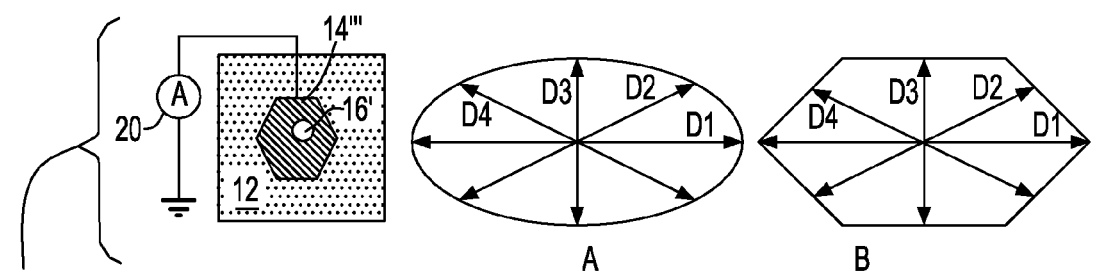

Within FIG. 6, two additional non-parallel linear directions are added interposed between the horizontal direction and the vertical direction that are illustrated in FIG. 5 for scanning of the substrate 12 and a feature 14''' (which now comprises a hexagon shape) with the charged beam 16'. Thus, within FIG. 6 four diameters D1, D2, D3 and D4 may be determined for the charged beam 16'. The diameters include a horizontal charged beam diameter D1, a vertical charged beam diameter D2 (that is less than the horizontal charged beam diameter D1) and two interposed charged beam diameters D3 and D4 (that are of an equal dimension interposed between the horizontal charged beam diameter D1 and the vertical charged beam diameter D2). As is illustrated in FIG. 6 this particular configuration of diameters D1, D2, D3 and D4 does not distinguish between an ellipse A and a hexagon B for a charged beam 16' aerial dimensional map.

Figure 7:
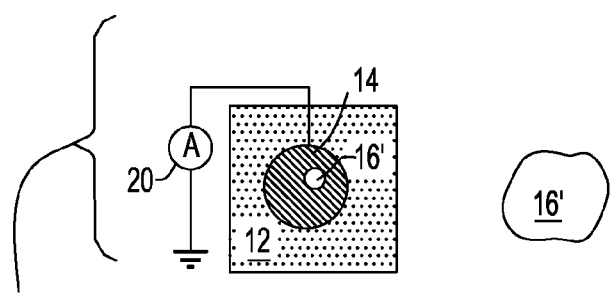

Finally, FIG. 7 illustrates a limiting example that considers a large number of non-parallel linear directions (i.e., perhaps about 180) for measuring current versus position response curves for the charged beam 16' when scanning the substrate 12 and the feature 14 that in accordance with FIG. 1 comprises a circular shape. As is disclosed above, an increased number of non-parallel linear directions allows for determination of a charged beam 16' aerial dimensional map A with enhanced precision and accuracy.

As is further illustrated within the schematic diagrams of FIG. 4 to FIG. 7, the particular shapes of the features 14', 14", 14''' or 14 do not limit the embodiment or the invention, since as noted above, a feature need in general only have dimensions larger than that of a charged beam whose aerial dimensional map is desired to be determined. However, as noted above, particular shapes of particular features may be desirable mated with an expected aerial dimensional map of a particular charged beam desired to be determined using the particular features.

The foregoing preferred embodiment of the invention is illustrative of the invention rather than limiting of the invention. Revisions and modifications may be made to structures, components and methods in accordance with the foregoing preferred embodiment, while still providing a charged beam apparatus and related method in accordance with the invention, further in accordance with the accompanying claims.

What is claimed is:

1. A method for determining an aerial dimensional map of a charged beam comprising:
   providing a test structure comprising a feature located upon a substrate, where the feature and the substrate have different electrical conductivity characteristics;
   scanning a charged beam in a plurality of non-parallel linear directions with respect to the feature and the substrate and measuring through at least one of the feature and the substrate a current as a function of a position of the charged beam for each of the plurality of non-parallel linear directions; and
   determining an aerial dimensional map of the charged beam from the measurement of the current versus the position of the charged beam for each of the plurality of non-parallel linear directions.

2. The method of claim 1 wherein the feature comprises a conductive material.

3. The method of claim 1 wherein the substrate comprises a conductive material.

4. The method of claim 1 wherein feature has a geometry selected from the group consisting of a triangle, a rectangle, a square, an other regular or irregular polyhedron, a regular or irregular non-polyhedron, an ellipse and a circle.

5. The method of claim 1 wherein:
   the charged beam has a nominal diameter from about 1 to about 5 nanometers; and
   the feature has a nominal diameter from about 5 to about 100 nanometers.

6. The method of claim 1 wherein the plurality of non-parallel linear directions includes from about 4 to about 180 mutually intersection linear directions.

7. The method of claim 1 wherein the determining the aerial dimensional map uses a difference in inflection points in each current versus charged beam position curve for each of the plurality of non-parallel linear directions.

8. The method of claim 1 wherein the charged beam comprises an electron beam.

* * * * *